United States Patent [19]

Mohri et al.

[11] Patent Number: 4,820,660
[45] Date of Patent: Apr. 11, 1989

[54] LIGHT TRANSMITTING CALCIUM PHOSPHATE GLASS-CERAMICS

[75] Inventors: Yoshio Mohri; Kinji Sano, both of Matsusaka, Japan

[73] Assignee: Central Glass Company, Limited, Ube, Japan

[21] Appl. No.: 136,377

[22] Filed: Dec. 22, 1987

[30] Foreign Application Priority Data

Dec. 26, 1986 [JP] Japan .................. 61-308828

[51] Int. Cl.$^4$ ............... C03C 10/02; C03C 10/06
[52] U.S. Cl. ................................ 501/8; 501/5; 501/10; 501/32; 501/63; 501/73; 501/77; 501/78
[58] Field of Search .............. 501/10, 32, 8, 5, 63, 501/73, 77, 78

[56] References Cited

U.S. PATENT DOCUMENTS

| | | | |
|---|---|---|---|
| 4,366,253 | 12/1982 | Yagi | 501/10 |
| 4,560,666 | 12/1985 | Yoshida | 501/10 |
| 4,643,982 | 2/1987 | Kasaga et al. | 501/10 |

FOREIGN PATENT DOCUMENTS

| | | |
|---|---|---|
| 242037 | 1/1987 | German Democratic Rep. |
| 61-141641 | 6/1986 | Japan . |
| 61-158841 | 7/1986 | Japan . |
| 62-123042 | 6/1987 | Japan . |

Primary Examiner—Mark L. Bell
Attorney, Agent, or Firm—Fleit, Jacobson, Cohn & Price

[57] ABSTRACT

A transparent, semitransparent or opaline glass-ceramics containing calcium phosphate crystals uniform and very fine in grain size is obtained by heat-treating a glass essentially comosed of 38–52 wt % of $SiO_2$, 4–16 wt % of $P_2O_5$, 6–18 wt % of $Al_2O_3$ (may partly be replaced by $La_2O_3$), 20–33 wt % of CaO (may partly be replaced by MgO, BaO, SrO and/or ZnO), 4–17 wt % of $ZrO_2$ (may partly be replaced by $TiO_2$) and 0–0.5 wt % of alkali metal oxide(s), wherein the molar ratio of $P_2O_5$ to $ZrO_2$ is not greater than 3:1, at a temperature above the transition temperature and below the softening temperature of the glass. This glass-ceramics is excellent in refractoriness, electrical insulation resistance, chemical resistance and mechanical strength and has a relatively high coefficient of thermal expansion.

7 Claims, No Drawings

LIGHT TRANSMITTING CALCIUM PHOSPHATE GLASS-CERAMICS

BACKGROUND OF THE INVENTION

This invention relates to a light transmitting glass-ceramics comprising fine crystals of calcium phosphate uniformly dispersed in a $SiO_2$-$Al_2O_3$-$ZrO_2$ base glass matrix.

Calcium phosphate glass-ceramics are attracting increasing interest particularly as biomaterials. Many of calcium phosphate glass-ceramics proposed until now have used glass compositions high in the content of $P_2O_5$. However, a glass composition containing a large amount of $P_2O_5$ is not easy to glassify, and in heat-treating the glass for crystallizing calcium phosphate it is often that growth of crystal grains becomes nonuniform by reason of significant development of phase separation of the glass. As a consequence mechanical strength of the obtained glass-ceramics is not so high as expected.

When the content of alkali in calcium phosphate glass-ceramics is increased, a question arises in biocompatability of the glass-ceramics because transfer of the alkali into the living body might disturb a physiological balance. Besides, the increased alkali adversely affects the heat resistance, electrical insulation resistance and chemical resistance of the glass-ceramics.

JP-A No. 61-141641 and JP-A No. 61-158841 relate to calcium phosphate glass-ceramics and show adding a small amount of $ZrO_2$ as an optical nucleating agent to a $SiO_2$-$Al_2O_3$-$P_2O_5$-CaO-MgO base or $SiO_2$-$P_2O_5$-CaO base glass composition. Including these $ZrO_2$-containing glass-ceramics none of calcium phosphate glass-ceramics proposed until now, as long as we know, allow visible light to pass therethrough.

SUMMARY OF THE INVENTION

It is an object of the present invention to provide a calcium phosphate glass-ceramics which is light-transmitting and possesses thermal, electrical and mechanical characteristics favorable for applications to wide uses in various fields.

According to the invention there is provided a light transmitting glass-ceramics, which comprises fine crystals of calcium phosphate crystallized from a glass so as to be uniformly dispersed in a glass matrix provided by the uncrystallized part of the glass. The glass comprises, expressed as oxides, 38–52 wt % of $SiO_2$, 4–16 wt % of $P_2O_5$, 20–33 wt % of a divalent metal oxide component which is at least one oxide selected from CaO, MgO, BaO, SrO and ZnO with the proviso that CaO amounts to at least 2/5 of this component, 6–18 wt % of a trivalent metal oxide component which is at least one oxide selected from $Al_2O_3$ and $La_2O_3$ with the proviso that $Al_2O_3$ amounts to at least ½ of this component, 4–17 wt % of a tetravalent metal oxide component which is at least one oxide selected from $ZrO_2$ and $TiO_2$ with the proviso that $ZrO_2$ amounts to at least ⅓ of this component, and 0–0.5 wt % of an alkali metal oxide component which is at least one oxide selected from $Na_2O$, $K_2O$ and $Li_2O$, and in this glass the molar ratio of $P_2O_5$ to the tetravalent metal oxide component is not greater than 3:1.

A glass-ceramics according to the invention is obtained by heat-treating a glass body of the above specified composition at a temperature above the transition temperature of the glass and below the softening temperature of the glass to thereby crystallize calcium phosphate, mostly tricalcium phosphate, sometimes together with a smaller amount of anorthite and/or wollastonite. The crystal grains are almost uniform in grain size, and the grain size is of the order of micrometer or smaller. Since the crystal grain size is close to the wavelengths of visible light the glass-ceramics is transparent or semitransparent, or becomes opaline by scattering of light passing therethrough. The tiny crystals are uniformly distributed in the glass-ceramics and occupy at least 10 wt %, and in some cases more than 50 wt %, of the glass-ceramics. The remaining part of the glass-ceramics is a $SiO_2$-$Al_2O_3$-$ZrO_2$ base glass ceramics which tightly fills up the interstices between the tiny crystals so that the glass-ceramics contains no foams or bubbles.

By virtue of such a tight structure, this glass-ceramics is high in mechanical strength and exhibits good resistance to acid alkali. The glass-ceramics is excellent also in surface smoothness because of very small grain size of the crystals.

In the present invention it is indispensable to use $ZrO_2$ as a nucleating agent in order that by the aforementioned heat treatment a very large number of calcium phosphate crystals may evolve in a uniformly very fine grain size and in a uniform distribution over the entire region of the heat-treated glass body. Needless to mention, $ZrO_2$ substitutes itself for $SiO_2$ and serves as a glass skeleton forming component.

To obtain a calcium phosphate glass-ceramics which is transparent, semitransparent or opaline, it is important that in the glass composition the molar ratio of $P_2O_5$ to $ZrO_2$ should not be greater than 3:1. Usually an opaline or semitransparent glass-ceramics is obtained when the molar ratio is between 3:1 and about 2.5:1, and a transparent glass-ceramics when the molar ratio is still lower. In view of such a tendency it is presumable that $ZrO_2$ acts not only as a nucleating agent but also as a conditioner which plays an important role in controlling the growth of the precipitated crystals.

$TiO_2$ behaves nearly similarly to $ZrO_2$. Accordingly it is permissible to replace not more than ⅔ of $ZrO_2$ in the glass composition by $TiO_2$. When $TiO_2$ too is used the molar ratio of $P_2O_5$ to ($ZrO_2+TiO_2$) must not be greater than 3:1 for obtaining a light transmitting calcium phosphate glass-ceramics.

The glass-ceramics according to the invention is excellent in heat resistance: its softening temperature is above 800° C. and in some cases exceeds 900° C. This glass-ceramics is excellent in electrical insulation resistance too since the content of alkali is very low or nil.

The thermal expansion coefficient of this glass-ceramics is relatively high and ranges from 60 to $90\times10^{-7}$/°C. That is, in the aspect of thermal expansion this glass-ceramics is close to alumina and some other ceramics and also to some metals (e.g. thermal expansion coefficient of iron is about $100\times10^{-7}$/°C.).

With respect to heat resistance, thermal expansion coefficient and electrical insulation resistance, some types of light transmitting alumina ceramics are comparable to the glass-ceramic according to the invention. However, in producing articles of such ceramics the raw materials must be conditioned very precisely and sintering of the green bodies needs to be performed at very high temperatures and under very strict control of temperature, so that the production needs advanced and complicated techniques and entails high cost. In the case of the glass-ceramics of the invention, glass bodies can easily be produced by using conventional glass melting and forming methods and can be transformed into glass-ceramics bodies by a simple heat treatment, so that the production cost is relatively low.

As a light transmitting material the glass-ceramics according to the invention is useful in, for example, optical disc substrates, bulbs represented by discharge tubes, substrates and windows of display devices, furnace windows and heat resistant windows in buildings. As a biomaterial this glass-ceramics can be used in artificial teeth and bones. As a heat refractory, electrically insulating, chemically stable and mechanically strong material, this glass-ceramics has wide uses in various fields. For example, it is useful as insulating substrates of electronic or optoelectronic devices, and such substrates can well be coated with either ceramics or metals. Also it is possible to use the glass-ceramics as a glazing material for coating or bonding ceramics substrates or metal substrates or as a cementing material for magnetic recording heads. Still further, the glass-ceramics can be used as a bonding or binding material for ceramics and metals: for example, for binding abrasive grains of grinding attachments. This glass-ceramics can be formed into fibers which are suitable for use as reinforcing fibers in FRP or GRC and for other various purposes.

DETAILED DESCRIPTION OF THE INVENTION

In the present invention it is essential to use a glass composition specified hereinbefore. The amounts of the respective components are specified for the following reasons.

If the amount of $SiO_2$ is less than 38 wt % the glass composition cannot easily be glassified, and at the stage of crystallization the crystals are liable to become nonuniform in grain size and to include coarse grains. If the amount of $SiO_2$ is more than 52 wt % it is difficult to accomplish crystallization of the glass to a sufficient extent.

At least 6 wt % of $Al_2O_3$ (or $Al_2O_3$ and $La_2O_3$ with the aforementioned proviso) is included in the glass composition for adjusting the viscosity of the molten glass and also for aiding crystallization of uniformly fine crystal grains. However, if the content of $Al_2O_3$ is more than 18 wt % precipitation of calcium phosphate crystals will be obstacled. It is preferred that the amount of this trivalent metal oxide component falls in the range from 8 to 16 wt %. $La_2O_3$ has the effect of further enhancing chemical resistance of the glass matrix of the glass-ceramics.

If the amount of $P_2O_5$ is less than 4 wt % or the amount of CaO (may patly be replaced by MgO, BaO, SrO and/or ZnO with the aforementioned proviso) is less than 20 wt %, crystallization of calcium phosphate becomes insufficient. If the amount of $P_2O_5$ is more than 16 wt % or the amount of CaO (the divalent metal oxide component) is more than 33 wt % the crystals are liable to become nonuniform and to include coarse grains. Both uniformity and fineness of the crystal grains become best when the amount of $P_2O_5$ is 4–14 wt % and the amount of the divalent metal oxide component is 23–30 wt %. The addition of ZnO tends to somewhat lower the softening temperature of the glass-ceramics, whereas the addition of BaO tends to considerably raise the softening temperature. Therefore, ZnO or BaO may selectively be used according to the intended use of the glass-ceramics.

The importance of including $ZrO_2$ (may partly be replaced by $TiO_2$ with the aforementioned proviso) was explained hereinbefore. If the content of $ZrO_2$ (the tetravalent metal oxide component) is less than 4 wt % the expected effects remain insufficient so that the crystal grains are liable to become nonuniform in grain size and to include coarse grains. If the content of the tetravalent metal oxide component is more than 17 wt % it becomes difficult to well melt the glass without using a special technique. Melting of the glass is very easy when the content of the tetravalent metal oxide is not more than 14 wt %. The molar ratio of $P_2O_5$ to the tetravalene metal oxide component must not be greater than 3:1 for the reasons explained hereinbefore.

Besides the above described essential components, the glass composition may contain fluorine, preferably in the form of $CaF_2$, for further easing melting of the glass or for reducing the surface tension of the molten glass to thereby promote foam refining. For such purposes it suffices that $F_2$ amounts to 0.1-1 wt % of the glass composition.

Alkali components such as $Na_2O$, $K_2O$ and/or $Li_2O$ are not necessary for a glass composition used in this invention since existence of alkali is unfavorable for heat resistance, electrical insulation resistance and chemical resistance of the glass. The total content of alkali metal oxides, including ones introduced as impurities, should not exceed 0.5 wt %. Though addition of $Li_2O$ is effective for further improvement in meltability and formability of the glass, addition of more than 0.5 wt % of $Li_2O$ is inhibited. Even in so-called alkaliless glasses (e.g. E-glass) it is usual to include a small amount of alkali for the sake of convenience in melting and forming the glass. In this view, glass compositions employed in this invention belong to alkaliless glasses.

It is rather preferable to add a small amount of $B_2O_3$ to the glass component to thereby further improve meltability without lowering electrical insulation resistance. The content of $B_2O_3$ should not exceed 3 wt % in order not to mar the heat resistance of the glass. It is undesirable to jointly use $Li_2O$ and $B_2O_3$ because of their synergetically adverse effects on the heat resistance.

A conventional clarifying agent such as $As_2O_3$ and/or $Sb_2O_3$ may optionally be added to the glass composition. It suffices to add 0.2-1 part by weight of clarifying agent to 100 parts by weight of the glass composition comprised of the above described components. In a practical sense, this means that the glass composition may contain up to 1 wt % of clarifying agent.

Raw materials for the glass-ceramics according to the invention are not particularly specified and can be selected from ones used in producing conventional glasses. For example, silica sand, zircon sand, alumina, aluminum metaphosphate and calcium carbonate may be used together with optional materials such as barium nitrate, magnesium oxide, zinc oxide, strontium oxide, lithium carbonate, calcium fluoride and/or arsenic oxide. A batch of raw materials is prepared according to the aimed composition of glass, and the batch is melted to obtain a clear melt of glass by heating in a pot furnace or a tank furnace for 2-6 hr at a suitable temperature which usually ranges from 1400° to 1550° C. The molten glass is formed into a desired shape by using one of conventional glass forming methods.

The formed glass is transformed into calcium phosphate glass-ceramics by a heat treatment in a suitable furnace. That is, the formed glass is maintained at a temperature above the transition temperature of the glass (from about 700° C. to about 850° C., depending on the glass composition) and below the softening temperature of the glass (from about 800° C. to about 900° C.) for several hours. Maintaining the glass at a temperature close to the transition temperature is effective for maximizing the number of the evolving crystal nuclei, whereas maintaining the glass at a temperature close to the softening temperature is effective for very uniform growth of the evolved crystals.

Also it is possible to obtain a glass-ceramics body having a tight structure by the steps of cooling the molten glass to obtain a solid glass mass, pulverizing the glass mass to obtain a frit consisting of fairly fine particles, and heat-treating the frit in a mold.

The invention is further illustrated by the following nonlimitative examples.

EXAMPLES 1–30

Table 1A shows thirty kinds of glass compositions employed in Examples 1 to 30 of the invention. Silica sand, zircon sand, aluminum metaphosphate, alumina and calcium carbonate were used as raw materials of the essential components of every glass. In most examples magnesium oxide and barium nitrate were used together with calcium carbonate, and in every example fluorite (calcium fluoride) was used as the source of fluorine and arsenic oxide as a clarifying agent. In some examples boric acid, lithium carbonate, titanium dioxide, zinc oxide, strontium oxide or lanthanum oxide was included in the raw materials. (In Table 1A the amount of $As_2O_3$ is indicated by parts by weight per 100 parts by weight of the total of the other components, and the amount of $Li_2O$ in Example 20 is in the same sense.)

In every example a batch of raw materials was made up as prescribed, and the batch was melted in a platinum crucible by heating in an electric furnace at a temperature in the range from 1400° to 1550° C. for 4–6 hr. The molten glass was cast on a steel plate and left cooling.

As a crystallizing treatment, the glass of each example was subjected to heat treatment in an electric furnace. The heat treatment comprised raising the temperature of the glass up to a predetermined level shown in Table 1A at a rate of 5° C./min, maintaining the glass at the predetermined temperature for 4 hr and cooling the treated glass in air. The thus heat-treated glass plate was subjected to X-ray diffraction analysis. In every example crystallization of tricalcium phosphate was detected and it was evident that the glass had turned into a glass-ceramics. In some examples crystallization of anorthite and/or wollastonite was also detected.

The degree of light transmittance of every glass-ceramics was valued by observation by the naked eye. The result was as shown in Table 1B, wherein Tp means being transparent and Tm being semitransparent and slightly cloudy. Then, a portion of each glass-ceramics was cut and machined into specimens in the shape of rod 5 mm in diameter and 20 mm in length to measure the transition temperature, softening temperature (yield temperature) and thermal expansion coefficient of the glass-ceramics with a thermal expansion tester. The results were as shown in Table 1B. As can be seen in the table, the glass-ceramics of every example was light-transmitting and possessed favorable thermal characteristics.

TABLE 1A

| | Glass Composition (wt %) | | | | | | | | | |
|---|---|---|---|---|---|---|---|---|---|---|
| | $SiO_2$ | $ZrO_2$ | $P_2O_5$ | $Al_2O_3$ | CaO | MgO | BaO | $F_2$ | $As_2O_3$ | other |
| Ex. 1 | 52 | 4 | 6 | 14 | 19.5 | 2 | 2 | 0.5 | 0.3 | — |
| Ex. 2 | 48 | 6 | 8 | 14 | 19.5 | 2 | 2 | 0.5 | 0.3 | — |
| Ex. 3 | 48 | 4 | 10 | 14 | 19.5 | 2 | 2 | 0.5 | 0.3 | — |
| Ex. 4 | 46 | 6 | 10 | 14 | 19.5 | 2 | 2 | 0.5 | 0.3 | — |
| Ex. 5 | 42 | 6 | 14 | 14 | 19.5 | 2 | 2 | 0.5 | 0.3 | — |
| Ex. 6 | 40 | 8 | 14 | 14 | 19.5 | 2 | 2 | 0.5 | 0.3 | — |
| Ex. 7 | 38 | 10 | 14 | 14 | 19.5 | 2 | 2 | 0.5 | 0.3 | — |
| Ex. 8 | 52 | 4 | 6 | 8 | 25.5 | 2 | 2 | 0.5 | 0.3 | — |
| Ex. 9 | 50 | 4 | 8 | 8 | 25.5 | 2 | 2 | 0.5 | 0.3 | — |
| Ex. 10 | 48 | 6 | 8 | 8 | 25.5 | 2 | 2 | 0.5 | 0.3 | — |
| Ex. 11 | 46 | 4 | 12 | 8 | 25.5 | 2 | 2 | 0.5 | 0.3 | — |
| Ex. 12 | 46 | 6 | 10 | 8 | 25.5 | 2 | 2 | 0.5 | 0.3 | — |
| Ex. 13 | 42 | 10 | 10 | 8 | 25.5 | 2 | 2 | 0.5 | 0.3 | — |
| Ex. 14 | 38 | 12 | 12 | 8 | 25.5 | 2 | 2 | 0.5 | 0.3 | — |
| Ex. 15 | 38 | 14 | 10 | 8 | 25.5 | 2 | 2 | 0.5 | 0.3 | — |
| Ex. 16 | 38 | 14 | 10 | 8 | 29.5 | — | — | 0.5 | 0.3 | — |
| Ex. 17 | 42 | 10 | 10 | 11 | 22.5 | 2 | 2 | 0.5 | 0.3 | — |
| Ex. 18 | 52 | 4 | 4 | 14 | 19.5 | 2 | 2 | 0.5 | 0.3 | $B_2O_3$ 2 |
| Ex. 19 | 50 | 4 | 6 | 16 | 19.5 | 2 | 2 | 0.5 | 0.3 | — |
| Ex. 20 | 52 | 4 | 6 | 14 | 19.5 | 2 | 2 | 0.5 | 0.3 | $Li_2O$ 0.5 |
| Ex. 21 | 48 | 6 | 8 | 14 | 19.5 | 2 | 2 | 0.5 | 0.3 | — |
| Ex. 22 | 48 | 4 | 8 | 14 | 19.5 | 2 | 2 | 0.5 | 0.3 | $TiO_2$ 2 |
| Ex. 23 | 48 | 2 | 8 | 14 | 19.5 | 2 | 2 | 0.5 | 0.3 | $TiO_2$ 4 |
| Ex. 24 | 48 | 6 | 8 | 14 | 15.5 | — | — | 0.5 | 0.3 | ZnO 8 |
| Ex. 25 | 46 | 6 | 8 | 14 | 15.5 | 2 | 8 | 0.5 | 0.3 | — |
| Ex. 26 | 48 | 6 | 8 | 14 | 15.5 | 8 | — | 0.5 | 0.3 | — |
| Ex. 27 | 46 | 6 | 10 | 14 | 14.5 | 2 | 2 | 0.5 | 0.3 | ZnO 5 |
| Ex. 28 | 46 | 6 | 10 | 14 | 9.5 | 2 | 2 | 0.5 | 0.3 | ZnO 10 |
| Ex. 29 | 48 | 6 | 8 | 14 | 14.5 | 2 | 2 | 0.5 | 0.3 | SrO 5 |
| Ex. 30 | 48 | 6 | 8 | 10 | 19.5 | 2 | 2 | 0.5 | 0.3 | $La_2O_3$ 4 |

TABLE 1B

| | Heat Treatment Temp. (°C.) | Glass-ceramics | | | |
|---|---|---|---|---|---|
| | | Thermal Expansion Coefficient ($\times 10^{-7}$/°C.) | Transition Temp. (°C.) | Softening Temp. (°C.) | Degree of Light Transmittance |
| Ex. 1 | 850 | 60 | 805 | 885 | Tp |
| Ex. 2 | 850 | 65 | 805 | 890 | Tp |
| Ex. 3 | 860 | 58 | 815 | 886 | Tm |

TABLE 1B-continued

| | Heat Treatment Temp. (°C.) | Glass-ceramics | | | |
|---|---|---|---|---|---|
| | | Thermal Expansion Coefficient ($\times 10^{-7}$/°C.) | Transition Temp. (°C.) | Softening Temp. (°C.) | Degree of Light Transmittance |
| Ex. 4 | 860 | 65 | 815 | 886 | Tp |
| Ex. 5 | 860 | 66 | 815 | 886 | Tm |
| Ex. 6 | 860 | 67 | 815 | 885 | Tm |
| Ex. 7 | 850 | 68 | 820 | 886 | Tp |
| Ex. 8 | 800 | 71 | 748 | 825 | Tp |
| Ex. 9 | 810 | 74 | 776 | 843 | Tm |
| Ex. 10 | 850 | | 790 | 885 | Tp |
| Ex. 11 | 850 | 77 | 793 | 889 | Tp |
| Ex. 12 | 850 | 74 | 801 | 891 | Tp |
| Ex. 13 | 840 | 78 | 802 | 874 | Tp |
| Ex. 14 | 860 | 80 | 823 | 898 | Tp |
| Ex. 15 | 870 | 75 | 819 | 916 | Tp |
| Ex. 16 | 870 | 81 | | 920 | Tp |
| Ex. 17 | 810 | | | 890 | Tp |
| Ex. 18 | 810 | | | 837 | Tp |
| Ex. 19 | 870 | 59.5 | 840 | 885 | Tp |
| Ex. 20 | 810 | 60 | 749 | 856 | Tp |
| Ex. 21 | 850 | 65 | 805 | 889 | Tp |
| Ex. 22 | 850 | 58 | 825 | 876 | Tp |
| Ex. 23 | 850 | | | 865 | Tp |
| Ex. 24 | 860 | 60 | 729 | 878 | Tp |
| Ex. 25 | 890 | | 848 | 962 | Tm |
| Ex. 26 | 850 | | | 880 | Tp |
| Ex. 27 | 800 | 59 | 770 | 837 | Tp |
| Ex. 28 | 770 | | 700 | 807 | Tp |
| Ex. 29 | 870 | | | 900 | Tp |
| Ex. 30 | 870 | | | 890 | Tp |

COMPARATIVE EXAMPLES 1-3

As Comparative Examples 1 to 3, three kinds of glass compositions not in accordance with the invention, as shown in Table 2, were tested. In Comparative Example 1 the content of $ZrO_2$ was very low, and the molar ratio of $P_2O_5$ to $ZrO_2$ was greater than 3:1. The glass composition of Comparative Example 2 was analogous to an example disclosed in JP-A No. 61-141641 and the glass composition of Comparative Example 3 was analogous to an example disclosed in JP-A No. 61-158841. Both of these two kinds of glass compositions were very high in the total content of CaO and MgO and somewhat higher than 3:1 in the molar ratio of $P_2O_5$ to $ZrO_2$.

The glasses of Comparative Examples 1-3 were produced by the same method as in Examples 1-30, and every glass was subjected to the same heat treatment as in Examples 1-30. The heat treatment temperature was 850° C. in Comparative Example 1 and 900° C. in Comparative Examples 2 and 3. I every case the heat-treated glass turned into a glass-ceramics, but it was not light-transmitting. In the glass-ceramics of Comparative Examples 2 and 3, cracks had appeared probably by reason of nonuniform precipitation of relatively coarse crystal grains during the crystallizing heat treatment.

TABLE 2

| | Glass Composition (wt %) | | | | | | | | | |
|---|---|---|---|---|---|---|---|---|---|---|
| | $SiO_2$ | $ZrO_2$ | $P_2O_5$ | $Al_2O_3$ | CaO | MgO | BaO | $F_2$ | $As_2O_3$ | other |
| Comp. Ex. 1 | 50 | 2 | 10 | 14 | 19.5 | 2 | 2 | 0.5 | 0.3 | — |
| Comp. Ex. 2 | 32.8 | 4 | 14 | 12.5 | 25.7 | 11 | — | — | — | — |
| Comp. Ex. 3 | 32.2 | 4 | 15.6 | — | 28.1 | 20.1 | — | — | — | — |

What is claimed is:

1. A light transmitting glass-ceramics, consisting essentially of a glass and fine crystals crystallized from the glass so as to be uniformly dispersed in the a glass matrix provided by the uncrystallized part of the glass, said fine crystals comprising crystals of calcium phosphate; said glass consisting essentially of, expressed as oxides, 38–52 wt % of $SiO_2$, 4–16 wt % of $P_2O_5$, 20–33 wt % of a divalent metal oxide component which is at least one oxide selected from the group consisting of CaO, MgO, BaO, SrO and ZnO with the proviso that CaO amounts to at least 2/5 of the divalent metal oxide component, 6–18 wt % of a trivalent metal oxide component which is at least one oxide selected from the group consisting of $Al_2O_3$ and $La_2O_3$ with the proviso that $Al_2O_3$ amounts to at least ½ of the trivalent metal oxide component, 4–17 wt % of a tetravalent metal oxide component which is at least one oxide selected from the group consisting of $ZrO_2$ and $TiO_2$ with the proviso that $ZrO_2$ amounts to at least ⅓ of the tetravalent metal oxide component, 0–0.5 wt % of an alkali metal oxide component which is at least one oxide selected from the group consisting of $Na_2O$, $K_2O$ and $Li_2O$, 0–1 wt % of fluorine, 0–3 wt % of $B_2O_3$, and 0–1 wt % of a clarifying agent selected from the group consisting of $As_2O_3$ and $Sb_2O_3$; the molar ratio of $P_2O_5$ to said tetravalent metal oxide component in said glass being not greater than 3:1.

2. A glass-ceramics according to claim 1, wherein said fine crystals occupy at least 10 wt % of the glass-ceramics.

3. A glass-ceramics according to claim 2, wherein said fine crystals further comprise crystals of anorthite crystallized from said glass.

4. A glass-ceramics according to claim 2, wherein said fine crystals further comprise crystals of wollastonite crystallized from said glass.

5. A glass-ceramics according to claim 1, wherein the content of $P_2O_5$ in said glass is 4–14 wt % and the content of said divalent metal oxide component in said glass is 23–30 wt %.

6. A glass-ceramics according to claim 5, wherein the content of said trivalent metal oxide component in said glass is 8–16 wt %.

7. A glass-ceramics according to claim 5, wherein the content of said tetravalent metal oxide component in said glass is 4–14 wt %.

* * * * *